(12) United States Patent
Kramer

(10) Patent No.: US 9,174,008 B1  
(45) Date of Patent: Nov. 3, 2015

(54) SYSTEM AND METHOD FOR FACILITATING PERCUTANEOUS INTRAVASCULAR ACCESS

(71) Applicant: Radu Kramer, Woodcliff Lake, NJ (US)

(72) Inventor: Radu Kramer, Woodcliff Lake, NJ (US)

(*) Notice: Subject to any disclaimer, the term of this patent is extended or adjusted under 35 U.S.C. 154(b) by 196 days.

(21) Appl. No.: 13/921,408

(22) Filed: Jun. 19, 2013

(51) Int. Cl.  
*A61M 5/00* (2006.01)  
*A61M 5/46* (2006.01)

(52) U.S. Cl.  
CPC .................................. *A61M 5/46* (2013.01)

(58) Field of Classification Search  
CPC ............ A61B 7/3401; A61B 2017/3445; A61M 5/32; A61M 5/329; A61M 5/46; A61M 2005/3201; A61M 25/0668; A61M 25/008  
See application file for complete search history.

(56) References Cited

U.S. PATENT DOCUMENTS

| | | | |
|---|---|---|---|
| 4,585,446 A | 4/1986 | Kempf | |
| 5,057,083 A | 10/1991 | Gellman | |
| 5,836,868 A | 11/1998 | Ressemann et al. | |
| 5,885,258 A | 3/1999 | Sachdeva et al. | |
| 6,090,072 A | 7/2000 | Kratoska et al. | |
| 6,102,933 A | 8/2000 | Lee et al. | |
| 6,210,370 B1 | 4/2001 | Chi-Sing et al. | |
| 7,144,386 B2 | 12/2006 | Korkor et al. | |
| 7,214,237 B2 | 5/2007 | Don Michael et al. | |
| 7,665,466 B2 | 2/2010 | Figulla et al. | |
| 7,959,595 B2 | 6/2011 | Melsheimer et al. | |
| 8,323,228 B2 | 12/2012 | DeFonzo et al. | |
| 2006/0036045 A1 | 2/2006 | Wilson et al. | |
| 2007/0244440 A1 | 10/2007 | Pal et al. | |
| 2008/0208160 A9 | 8/2008 | Mawad et al. | |
| 2008/0275300 A1* | 11/2008 | Rothe et al. | 600/129 |
| 2009/0292272 A1* | 11/2009 | McKinnon | 604/523 |

* cited by examiner

*Primary Examiner* — Rebecca E Eisenberg  
(74) *Attorney, Agent, or Firm* — Arthur Jacob (57) ABSTRACT

A system and method facilitate percutaneous intravascular access while militating against unwanted penetration of the accessed blood vessel. A small diameter access tube includes a terminal segment comprised of a shape memory polymer and configured to flare outwardly toward a larger diameter orifice. The configuration of the terminal segment is modified to taper toward the insertion point of an internal insertion needle for facilitating insertion of the access tube into a blood vessel. Subsequent to insertion, the access tube is advanced relative to the insertion needle which then is retracted, and the terminal segment is allowed to return to the flared configuration so that fluid flow through the access tube is facilitated.

23 Claims, 7 Drawing Sheets

FIG. 1

PRIOR ART

FIG. 2

PRIOR ART

SYSTEM AND METHOD FOR FACILITATING PERCUTANEOUS INTRAVASCULAR ACCESS

The present invention relates generally to attaining percutaneous intravascular access and pertains, more specifically, to facilitating percutaneous intravascular access while militating against injury to the accessed blood vessel, including unwanted penetration of the blood vessel.

A very wide variety of currently-practiced medical procedures require intravascular access, typically for the establishment of a fluid flow through a needle introduced percutaneously into a blood vessel, or a graft, either for administering or withdrawing fluids. for example, a patient undergoing hemodialysis will require, over time, multiple procedures during which hemodialysis needles are introduced, percutaneously, to gain vascular access. Repeated needle use can result in chronic repetitive injury, leading to such undesirable consequences a venous stenosis. Moreover, the relatively large diameter needles required to accommodate the volumetric rate of flow desired in conducting hemodialysis requires a corresponding large incursion into a near wall portion of a blood vessel being accessed and increases the likelihood of an unwanted penetration at an opposite far wall portion of the accessed blood vessel upon insertion of a dialysis needle. Such penetration leads to infiltration, which actually is bleeding related to miscannulation, complicated by the formation of a hematoma surrounding the hemodialysis access, resulting in compression of the blood vessel or graft and possible stenosis, requiring surgical intervention for access revision. Further, percutaneous insertion of a larger diameter needle requires a larger opening at the insertion site, resulting in patient discomfort, longer healing times, and an increased risk of infection.

The present invention provides a system and method for accomplishing percutaneous intravascular access while avoiding the drawbacks outlined above. As such, the present invention attains several objects and advantages, some of which are summarized as follows: Enables minimally invasive percutaneous intravascular access for establishing a requisite volumetric flow rate of fluid into or out of an accessed blood vessel, while militating against such consequences as injury to or even an unwanted penetration of the blood vessel wall; accomplishes a requisite volumetric flow rate through insertion of a relatively small diameter, flexibly conformable intravascular access tube, while avoiding a larger access opening at an insertion site; reduces the risk of injury to an accessed blood vessel; reduces the risk of complications leading to a requirement for hospital admission to accomplish a surgical access revision; reduces the need, in a hemodialysis procedure, to make up for dialysis time lost as a result of infiltration; reduces the risk of infection; improves patient comfort and satisfaction; reduces the size of an access opening at an insertion site, and an incursion at a blood vessel access site without compromising a desired volumetric rate of blood flow; increases the accuracy of placement of an insertion needle or access tube in attaining intravascular access; avoids leakage at an insertion site, with a concomitant reduction in blood loss and the risk of spreading blood-borne infectious diseases from a patient to attending medical personnel, as well as to others; enhances and accelerates healing at the insertion site; facilitates an intravascular access procedure for added effectiveness with increased ease.

The above objects and advantages, as well as further objects and advantages, are attained by the present invention which may be described briefly as a system for facilitating percutaneous intravascular access while militating against unwanted penetration of an accessed blood vessel, the system comprising: an insertion needle having a given diameter and terminating in an insertion point; and an access tube having a tubular wall with an outside diameter, a proximal end, a distal terminal end, and an internal passage having a nominal internal diameter complementary to the given diameter of the insertion needle for reception of the insertion needle within the access tube, with the insertion needle extending to the terminal end; the tubular wall including at least a terminal segment comprised of a shape memory polymer, the terminal segment having a prescribed length extending to the terminal end of the access tube and being conformable between a native configuration wherein the internal passage increases radially outwardly along the terminal segment toward the terminal end to provide the internal passage with a gradually expanded configuration including an orifice at the terminal end having an internal diameter greater than the nominal internal diameter, and a modified configuration wherein the terminal segment is substantially contiguous with the insertion needle along the prescribed length and the terminal end is juxtaposed with the insertion point of the insertion needle to facilitate insertion while militating against unwanted penetration; the terminal segment being transformable in response to an external condition to return from the modified configuration to the native configuration such that upon insertion into the blood vessel of the insertion point and the juxtaposed terminal segment in the modified configuration and subsequent retraction of the insertion needle from the access tube, the terminal segment will return to the native configuration and fluid flow through the internal passage will be facilitated by the gradually expanded configuration of the internal passage of the tubular wall of the access tube.

In addition, the present invention provides a method for facilitating percutaneous intravascular access while militating against unwanted penetration of an accessed blood vessel, the method comprising: providing an insertion needle having a given diameter and terminating in an insertion point; providing an access tube having a tubular wall with a terminal end, an outside diameter and an internal passage with a nominal internal diameter complementary to the given diameter of the insertion needle; constructing at least a terminal segment of the tubular wall of the access tube adjacent the terminal end to be comprised of a shape memory polymer, with the terminal segment having a prescribed length and a native configuration wherein the internal passage increases radially outwardly along the terminal segment toward the terminal end to provide the internal passage with a gradually expanding configuration including an orifice at the terminal end having an internal diameter greater than the nominal internal diameter; modifying the terminal segment to conform the terminal segment to a modified configuration wherein the terminal segment will be substantially contiguous with the insertion needle along the prescribed length and the terminal end will be juxtaposed with the penetrating point to facilitate insertion while militating against unwanted penetration; locating the insertion needle within the internal passage of the access tube with the terminal end of the access tube juxtaposed with the insertion point of the insertion needle when the terminal segment is in the modified configuration; inserting the insertion point and the juxtaposed terminal segment in the modified configuration into a blood vessel until the insertion point is just within the blood vessel; advancing the access tube into the blood vessel while maintaining the insertion needle substantially stationary; subsequently retracting the insertion needle from the access tube; and effecting transformation of the terminal segment in response to an external condition to return the terminal segment from the modified configuration to the native configuration such that the terminal segment will return to the native configuration, placed within the accessed blood vessel, and volumetric fluid flow through the internal passage will be facilitated by the radially outwardly increasing configuration of the internal passage of the tubular wall of the access tube.

Further, the present invention includes an improvement in a system for facilitating percutaneous intravascular access by an insertion needle having a given diameter and terminating in an insertion point, while militating against unwanted penetration of an accessed blood vessel, the improvement comprising: an access tube having a tubular wall with an outside diameter, a proximal end, a distal terminal end, and an internal passage having a nominal internal diameter complementary to the given diameter of the insertion needle for reception of the insertion needle within the access tube, with the insertion needle extending to the terminal end; the tubular wall including at least a terminal segment comprised of a shape memory polymer, the terminal segment having a prescribed length extending to the terminal end of the access tube and being conformable between a native configuration wherein the internal passage increases radially outwardly along the terminal segment toward the terminal end to provide the internal passage with a gradually expanded configuration including an orifice at the terminal end having an internal diameter greater than the nominal internal diameter, and a modified configuration wherein the terminal segment will be substantially contiguous with the insertion needle along the prescribed length and the terminal end will be juxtaposed with the insertion point of the insertion needle to facilitate insertion while militating against unwanted penetration; the terminal segment being transformable in response to an external condition to return from the modified configuration to the native configuration such that upon insertion into the blood vessel of the terminal segment in the modified configuration, the terminal segment will return to the native configuration and fluid flow through the internal passage will be facilitated by the gradually expanded configuration of the internal passage of the tubular wall of the access tube.

The invention will be understood more fully, while still further objects and advantages will become apparent, in the following detailed description of preferred embodiments of the invention illustrated in the accompanying drawing, in which.

Figure 1:
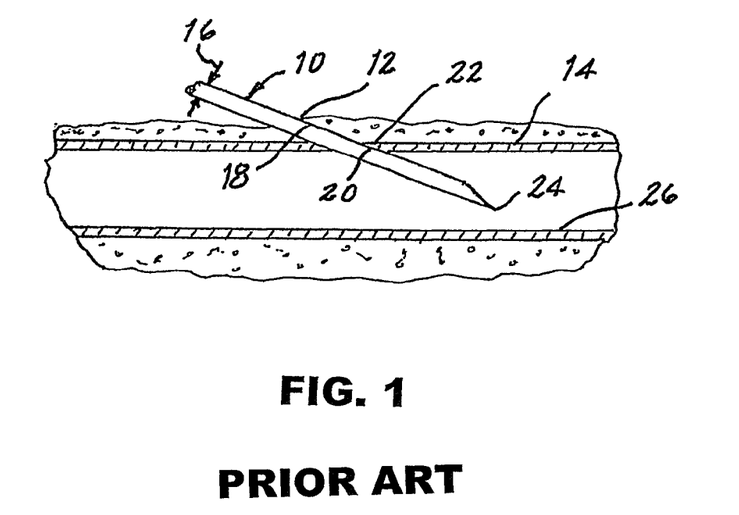
FIG. 1 is a largely diagrammatic illustration of a stage in an intravascular access procedure being carried out in accordance with the prior art.

Referring now to the drawing, and especially to FIG. 1 thereof, there is depicted a step in a currently conventional hemodialysis procedure wherein a hemodialysis needle 10 is shown being inserted percutaneously at an insertion site 12 into a blood vessel 14. In this instance, insertion site 12 is a venous site, and needle 10 is provided with a diameter 16 great enough to establish a volumetric flow rate of blood from blood vessel 14 commensurate with the requirements of the hemodialysis procedure. The insertion opening 18 at insertion site 12 is made large enough to accommodate the reception of diameter 16 of needle 10, as is the incursion 20 in near wall portion 22 of blood vessel 14, both of which opening 18 and incursion 20 are accomplished by insertion point 24 of needle 10. Typically, needle 10 will be of a size having a magnitude of about a fourteen gage needle in order to provide an adequate volumetric flow rate.

Figure 2:
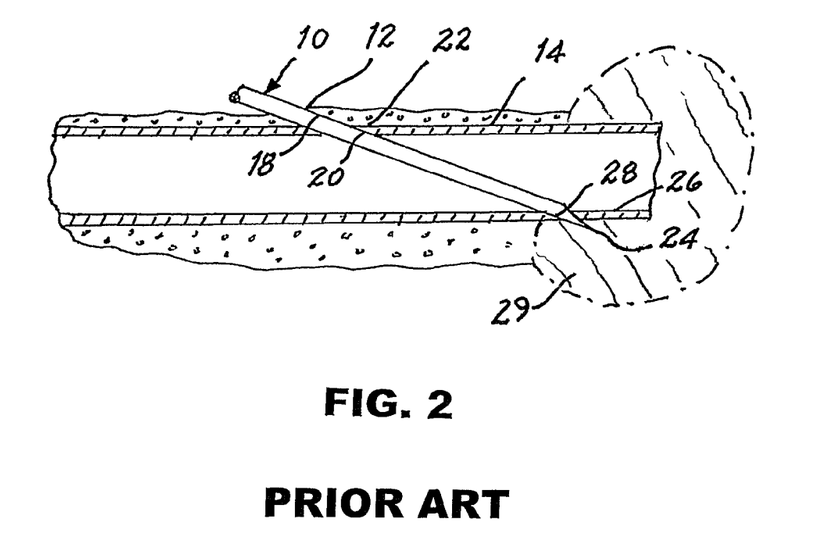
FIG. 2 is a depiction of an unwanted penetration made possible by the procedure illustrated in FIG. 1.

The necessity for the use of a needle 10 of a large size, relative to the size of the accessed blood vessel 14, has led to certain drawbacks, among which are injury to the blood vessel and possible unwanted penetration of the blood vessel wall. Mere contact of the insertion point 24 of the needle 10, for example, with a far wall portion 26 of the blood vessel 14 can cause injury that eventually may lead to the undesirable consequence of stenosis of the blood vessel 14. With reference to FIG. 2, of even greater concern is the possibility of penetration of the far wall portion 26, as illustrated at 28, causing damage to the blood vessel 14, as well as highly undesirable leakage at the site of such penetration, leading to infiltration and related complications, as depicted diagrammatically at 29.

Figure 3:
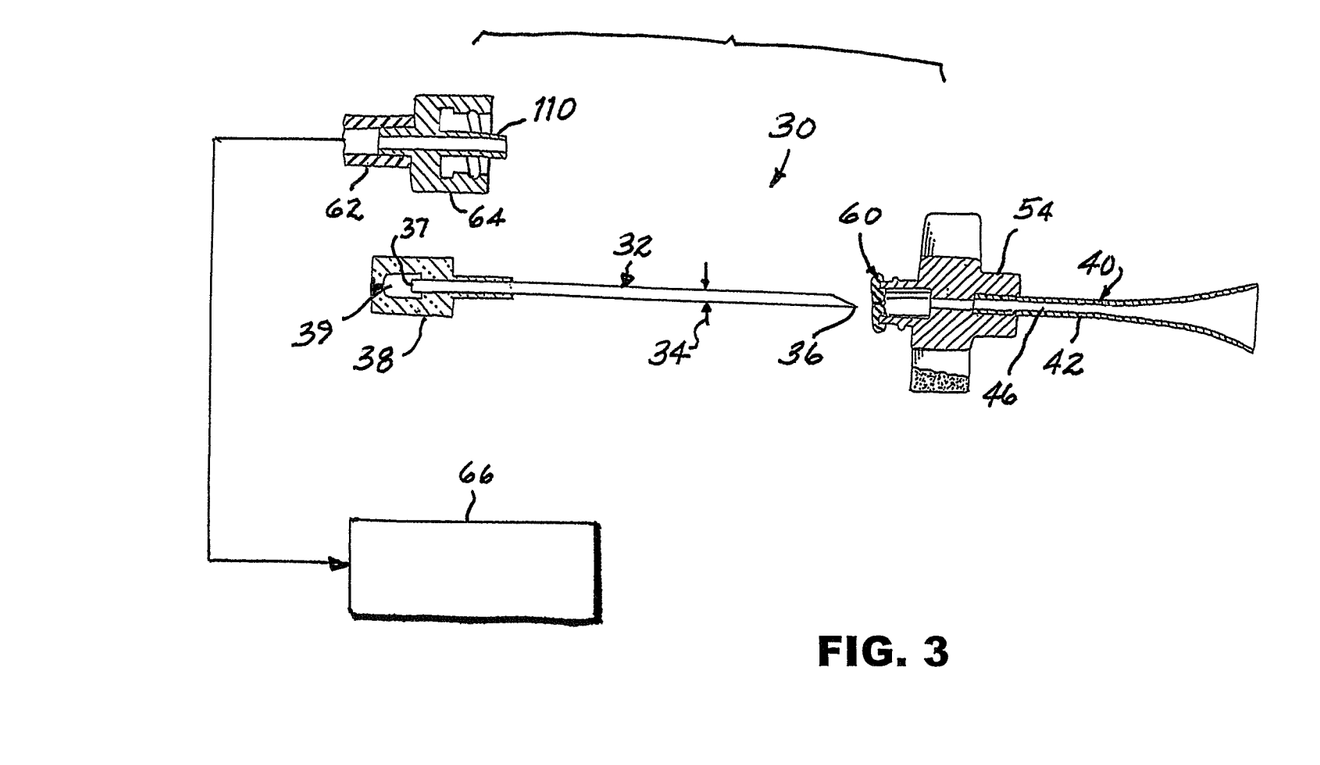
FIG. 3 is an exploded, elevational view, partially diagrammatic, and reduced in scale, of a system constructed in accordance with the present invention for use in a method of accomplishing intravascular access in accordance with the present invention.
Figure 4:
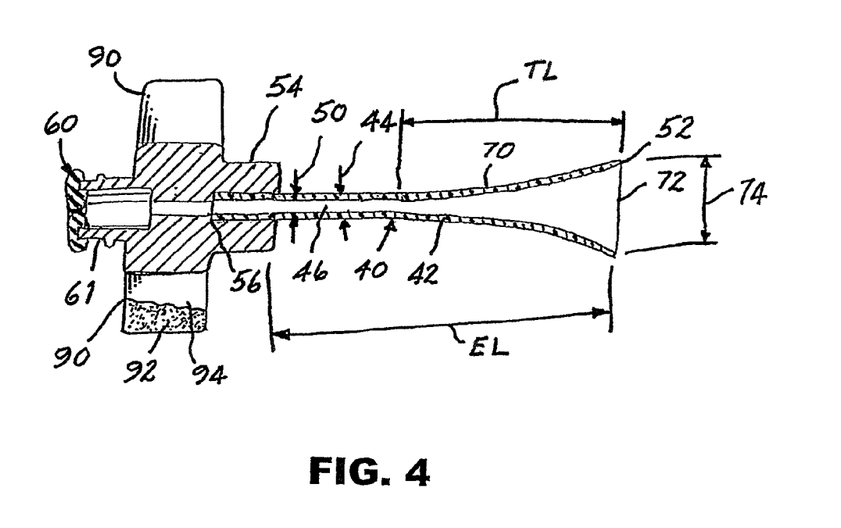
FIG. 4 is a longitudinal cross-sectional view of a component part of the system of FIG. 3.

Turning now to FIGS. 3 and 4, a system constructed in accordance with the present invention is shown at 30 and is seen to include an insertion needle 32 having a very small given diameter 34 and terminating at an insertion point 36. Insertion needle 32 is hollow, and a finger grip 38 is affixed to insertion needle 32 adjacent the end 37 opposite insertion point 36. Finger grip 38 is constructed of a transparent material and includes an inner chamber 39 communicating with hollow insertion needle 32, for purposes set forth below.

An access tube 40 has a tubular wall 42 with an extended length EL, an outside diameter 44 and an internal passage 46. Internal passage 46 has a nominal internal diameter 50 complementary to the given diameter 34 of the insertion needle 32, and access tube 40 terminates at a distal terminal end 52. A fitting 54 is integral with access tube 40 adjacent a proximal end 56 opposite terminal end 52. Fitting 54 is configured for including a check valve 60 communicating serially with internal passage 46, and includes a neck 61 arranged for being joined with an external delivery tube 62, by means of a coupling 64. As illustrated diagrammatically, external delivery tube 62 is connected to a processing apparatus which, for illustrative purposes, comprises a dialysis apparatus 66 for receiving and processing blood to be delivered through access tube 40, to delivery tube 62, in a now conventional manner.

Tubular wall 42 of access tube 40 includes at least a terminal segment 70 having a prescribed length TL extending to the terminal end 52 of the access tube 40, the terminal segment 70 being constructed so as to be comprised of a shape memory polymer. In an original, or native configuration, illustrated in FIGS. 3 and 4, internal diameter 50 of internal passage 46 increases gradually along terminal segment 70 and preferably is flared radially outwardly toward terminal end 52 to provide internal passage 46 with an expanding configuration terminating at an orifice 72 having an internal diameter 74 at the terminal end 52 substantially greater than the nominal internal diameter 50 of internal passage 46, for purposes to be described more fully below.

Figure 5:
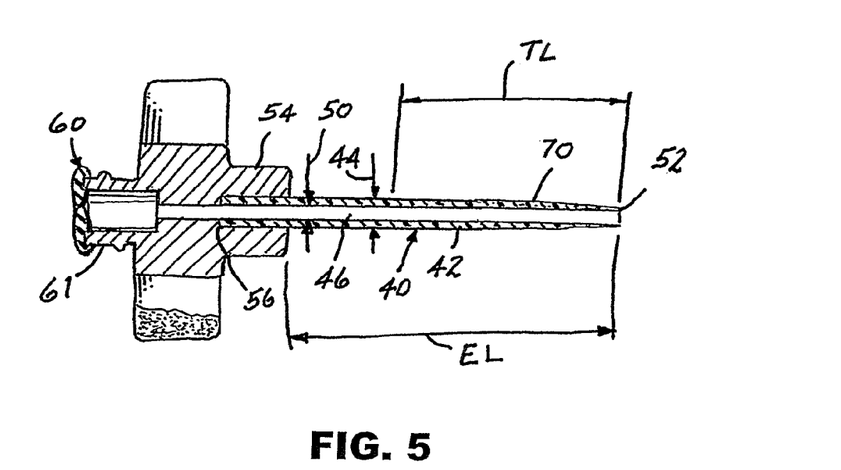
FIG. 5 is a longitudinal cross-sectional view of the component part illustrated in FIG. 4, and shown modified in accordance with the present invention.
Figure 6:
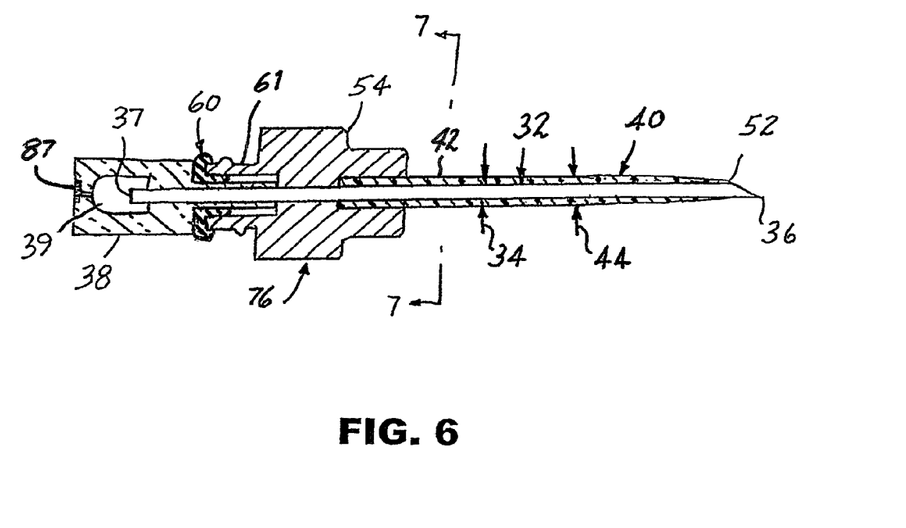
FIG. 6 is a longitudinal cross-sectional view of an assembly of component parts for use in connection with a procedure conducted in accordance with the present invention.

As shown in FIG. 5, the configuration of terminal segment 70 is subjected to modification so as to depart from the native configuration, illustrated in FIG. 4, and assume a modified configuration, as shown in FIG. 5, in which terminal segment 70 will be rendered contiguous with insertion needle 32, along the prescribed length TL, and terminal end 52 will be juxtaposed with the insertion point 36 of insertion needle 32, upon location of the insertion needle 32 within the terminal segment 70, as seen in FIG. 6. Modification of a shape memory polymer from a native, or original, configuration to a modified configuration is well known in the art of working with shape memory polymers. In the preferred embodiment illustrated in FIGS. 3 and 4, length TL of the terminal segment 70 occupies about two-thirds of the extended length EL of tubular wall 42. Upon modification of the configuration of terminal segment 70 to the illustrated modified configuration, terminal segment 70 is tapered, preferably along the length TL essentially to fair into insertion point 36 of insertion needle 32, as shown in FIG. 6. Once access tube 40 and insertion needle 32 are placed in an assembled state, as seen at 76 in FIGS. 6 and 7, the assembly 76 is ready for insertion into a selected blood vessel. Toward that end, the given diameter 34 of insertion needle 32 is very small, in the order of that of a sixteen to eighteen gage needle, and the outside diameter 44 of access tube 40 is not very much greater, so that the assembly 76 consisting of insertion needle 32 and access tube 40 remains very small in diameter. It is to be understood that the term "blood vessel", as used herein, denotes a graft in common use in connection with the procedures described herein, as well as a natural blood vessel.

Figure 8:
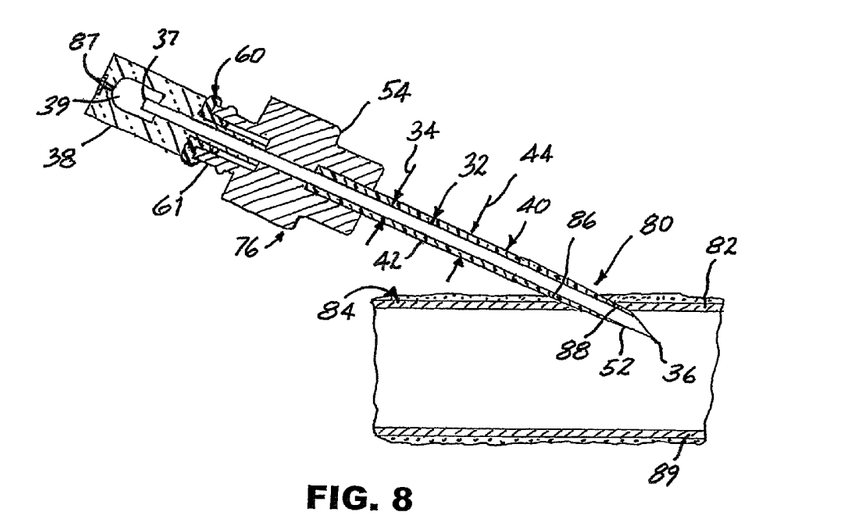
FIG. 8 is a somewhat diagrammatic view showing a step in the procedure being conducted in accordance with the present invention.

Referring now to FIGS. 8 through 12, the insertion needle 32 and access tube 40, assembled into assembly 76, as described above, with terminal segment 70 in the modified configuration, are inserted, percutaneously, at an insertion site, shown in the form of a venous insertion site 80, just until the wall 82 of a selected blood vessel 84 is pierced, as seen in FIG. 8. The very small given diameter 34 of insertion needle 32 and the small outside diameter 44 of access tube 40 enable a minimally invasive insertion, with a concomitant small insertion opening 86 at insertion site 80, and a very small incursion 88 at the wall 82 of blood vessel 84. Insertion needle 32 is hollow, so that upon insertion, as described, a small amount of blood can flow through needle 32 and into chamber 39 of finger grip 38, such flow being facilitated by a vent arrangement at 87, providing a visual indication that the wall 82 of blood vessel 84 has indeed been pierced and the terminal end 52 of access tube 40 is placed within blood vessel 84. This visual indication, appearing immediately upon entry into blood vessel 84, signals the observer to discontinue advancement of the assembly 76, thereby enabling avoidance of any deleterious contact between the insertion point 36 of insertion needle 32 and the interior of wall 82 of the blood vessel 84, and especially militating against unwanted penetration of wall portion 89 of the wall 82, opposite incursion 88. At the same time, check valve 60 prevents any leakage of blood between the insertion needle 32 and neck 61 of fitting 54.

Figure 7:
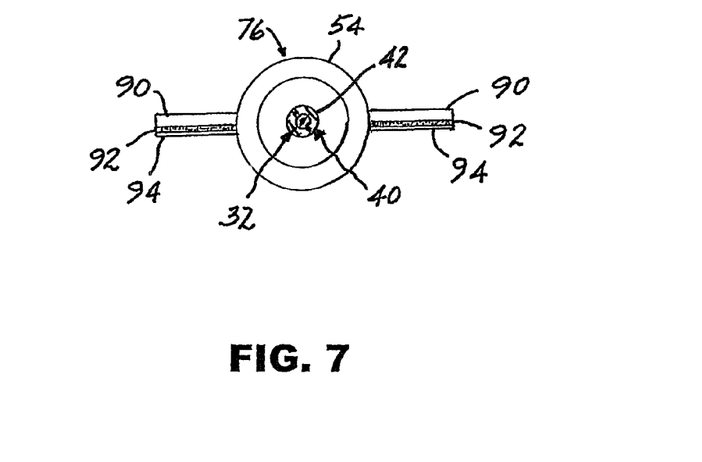
FIG. 7 is a cross-sectional view taken along line 7-7 of FIG. 6.
Figure 9:
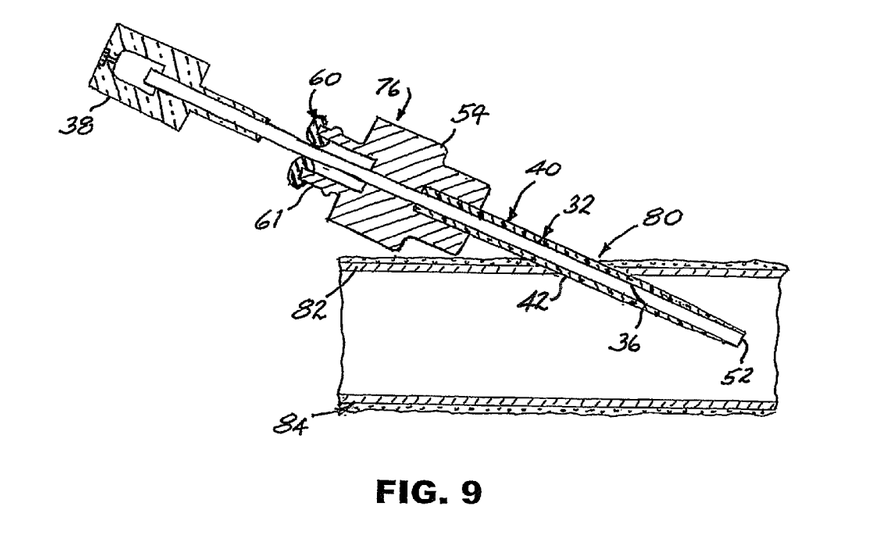
FIG. 9 is a view similar to FIG. 8 and showing a further step in the procedure.
Figure 10:
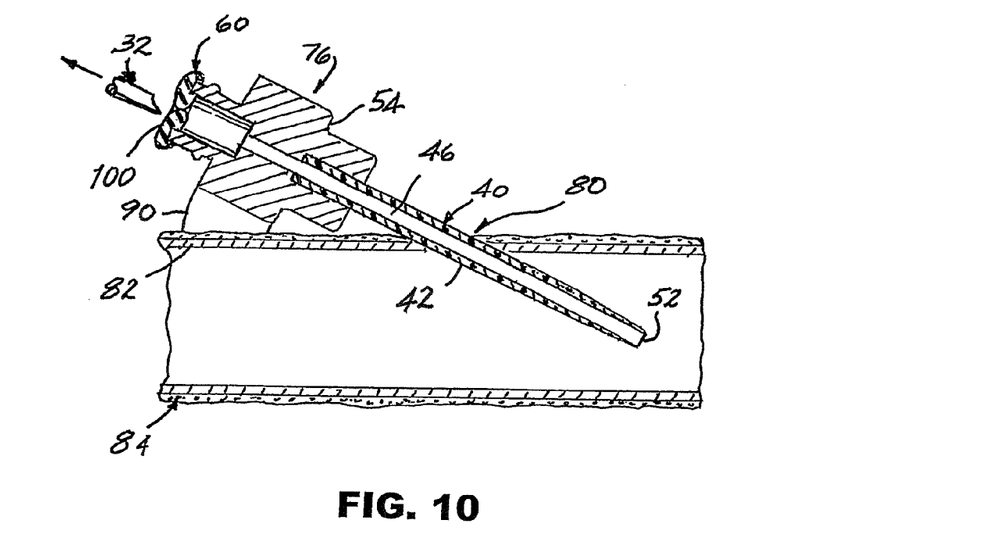
FIG. 10 is another similar view, showing a still further step in the procedure.

Once assembly 76 is in place, just within blood vessel 84, as seen in FIG. 8, access tube 40 is advanced, along with fitting 54, relative to insertion needle 32, while insertion needle 32 is held essentially stationary, as depicted in FIG. 9. The very flexible nature of the thin and resilient access tube 40 places terminal segment 70 well within the blood vessel 84, while the insertion point 36 of the now stationary insertion needle 32 is maintained well away from contact with wall 82 of blood vessel 84, and especially away from opposite wall portion 89. Then, the insertion needle 32 is withdrawn from the access tube 40, and from fitting 54, as seen in FIG. 10, allowing check valve 60 to close so that any blood which may follow the removal of insertion needle 32 from internal passage 46 of access tube 40 will be stopped at the check valve 60. To that end, check valve 60 includes a resilient closure member 100 that permits passage of insertion needle 32 through check valve 60, while maintaining a seal at insertion needle 32, and then closes off any escape of blood that might follow the insertion needle 32 as the insertion needle 32 is withdrawn from the check valve 60. With the access tube 40 fully inserted into blood vessel 84, fitting 54 is secured in place on the patient by securing tabs 90 provided integral with the fitting 54, and thus integral with access tube 40, so as to be conveniently available to the practitioner conducting the procedure. As seen in FIGS. 4 and 7, each securing tab 90 carries a layer 92 of a pressure-sensitive adhesive over which there is placed a release sheet 94. The practitioner merely need peel away the release sheet 94 to expose the adhesive layer 92 and then affix the securing tab 90 in place.

Figure 11:
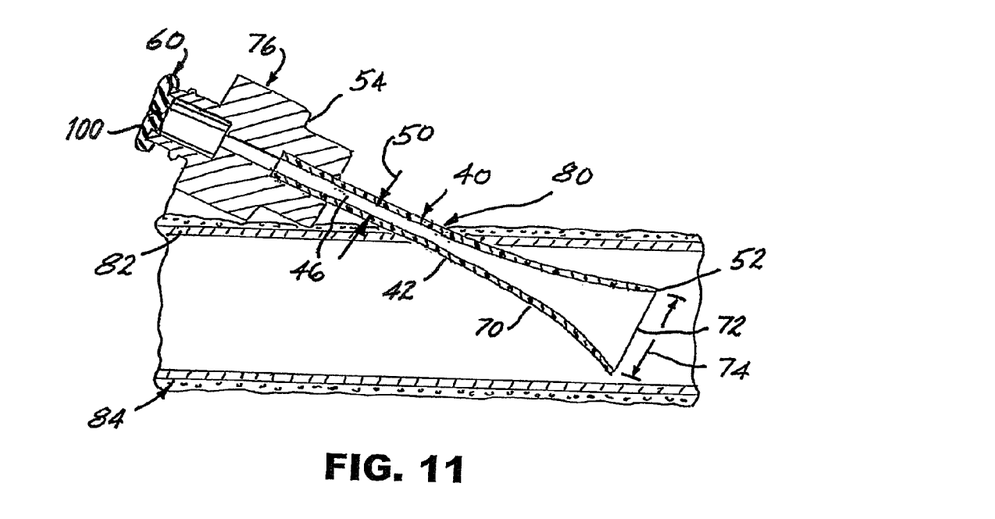
FIG. 11 is still another similar view, showing yet another step in the procedure.

With the check valve 60 so closed, blood flow out of blood vessel 84, through the access tube 40 is precluded. As described above, the shape memory polymer of terminal segment 70 of access tube 40 is transformable in response to external conditions such that a component part created in an original, native configuration can then be modified to create a modified configuration and, upon exposure to such external conditions, the component part will return from the modified configuration to the original, native configuration. Thus, with reference to FIG. 11, having been exposed to the external conditions encountered within the blood vessel 84, namely, the raised temperature and humidity existing within the blood vessel 84, terminal segment 70 has responded to those conditions and has returned from the modified configuration to the original, native configuration, as seen in FIG. 11, wherein the terminal segment 70 has reverted to the configuration in which the internal diameter 50 of internal passage 46 increases gradually to that of the orifice 72 at the terminal end 52 which itself has reverted to the original internal diameter 74. In the preferred construction, internal diameter 74 of orifice 72 is at least about twice the outside diameter 44 of access tube 40, and the native configuration provides a funnel-like construction that enables an increase in the volumetric flow rate to a desirable level. In terms of gage size, the flared configuration leading to orifice 72 provides a volumetric flow rate through internal passage 46 that is the equivalent of a gage size approximately twice that of outside diameter 44 of access tube 40. For example, an access tube 40 having a size equivalent to a sixteen to eighteen gage needle will, upon presenting the flared configuration leading to enlarged orifice 72, attain a volumetric rate of flow ordinally attained by a fourteen to fifteen gage needle.

Figure 12:
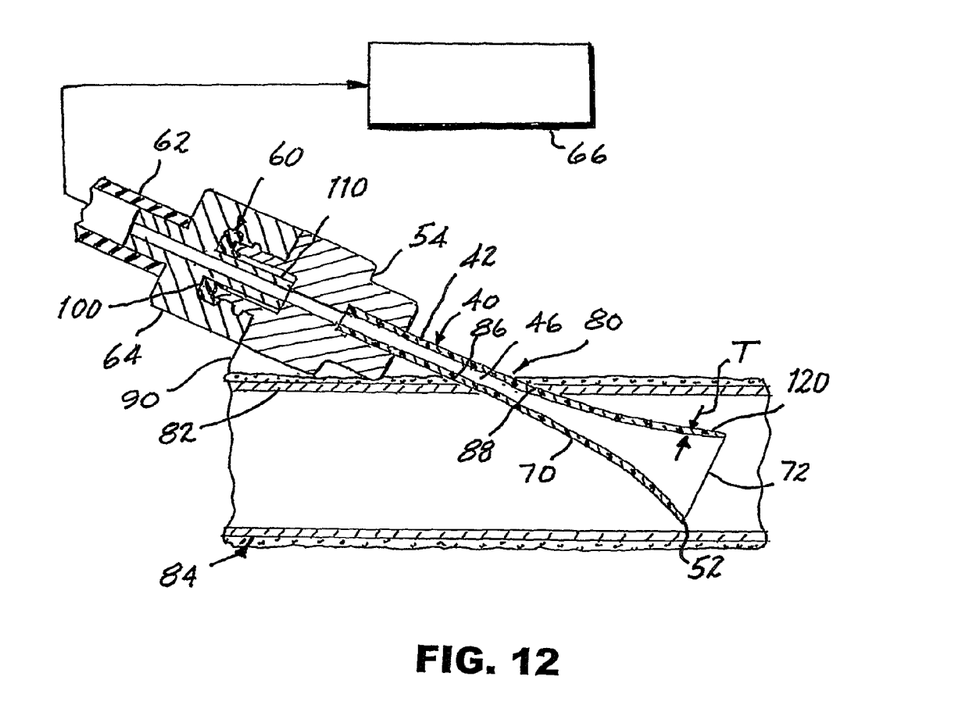
FIG. 12 is yet another similar view, showing another step in the procedure.

Thus, upon affixing coupling 64 to the fitting 54, as seen in FIG. 12, nose 110 of the coupling 64 will open closure member 100 and, while maintaining a seal along nose 110, will permit the flow of blood from access tube 40 into delivery tube 62 for delivery to dialysis apparatus 66, with the native configuration facilitating a requisite volumetric flow rate through the initially much smaller access tube 40. Fluid flow is facilitated further by the contour configuration of the tubular wall 42 along the flared configuration, wherein the thickness T of the tubular wall 42 along the flared configuration is reduced gradually toward the terminal end 52, thereby establishing a smooth and unrestricted path for an accelerated flow into the access tube 40.

Upon completion of the dialysis procedure, the flexible nature of the tubular wall 42 of access tube 40, together with the contour configuration of the flared terminal segment 70 and a thinned wall section 120 established by the diminishing thickness T along the flared configuration, enables a ready collapse of the flared configuration for ease of withdrawal of the access tube 40 through the minimal insertion opening 86, as well as the incursion 88, at the insertion site 80. The very small opening 86, and the very small incursion 88, will minimize patient discomfort while promoting healing and militating against infection.

It will be seen that the present invention attains all of the objects and advantages summarized above, namely: Enables minimally invasive percutaneous intravascular access for establishing a requisite volumetric flow rate of fluid into or out of an accessed blood vessel, while militating against such consequences as injury to or even an unwanted penetration of the blood vessel wall; accomplishes a requisite volumetric flow rate through insertion of a relatively small diameter, flexibly conformable intravascular access tube, while avoiding a larger access opening at an insertion site; reduces the risk of injury to an accessed blood vessel; reduces the risk of complications leading to a requirement for hospital admission to accomplish a surgical access revision; reduces the need, in a hemodialysis procedure, to make up for dialysis time lost as a result of infiltration; reduces the risk of infection; improves patient comfort and satisfaction; reduces the size of an access opening at an insertion site, and an incursion at a blood vessel access site without compromising a desired volumetric rate of blood flow; increases the accuracy of placement of an insertion needle or access tube in attaining intravascular access; avoids leakage at an insertion site, with a concomitant reduction in blood loss and the risk of spreading blood-borne infectious diseases from a patient to attending medical personnel, as well as to others; enhances and accelerates healing at the insertion site; facilitates an intravascular access procedure for added effectiveness with increased ease.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. A system for facilitating percutaneous intravascular access while militating against unwanted penetration of an accessed blood vessel, the system comprising:
   an insertion needle having a given diameter and terminating in an insertion point; and
   an access tube having a tubular wall with an outside diameter, a proximal end, a distal terminal end, and an internal passage having a nominal internal diameter complementary to the given diameter of the insertion needle for reception of the insertion needle within the access tube, with the insertion needle extending to the terminal end;
   the tubular wall including at least a terminal segment comprised of a shape memory polymer, the terminal segment having a prescribed length extending to the terminal end of the access tube and being conformable between
   a native configuration wherein the internal passage increases radially outwardly along the terminal segment toward the terminal end to provide the internal passage with a gradually expanded configuration including an orifice at the terminal end having an internal diameter greater than the nominal internal diameter, and
   a modified configuration wherein the terminal segment is substantially contiguous with the insertion needle along the prescribed length and the terminal end is juxtaposed with the insertion point of the insertion needle to facilitate insertion while militating against unwanted penetration;
   the terminal segment being transformable in response to an external condition to return from the modified configuration to the native configuration such that upon insertion into the blood vessel of the insertion point and the juxtaposed terminal segment in the modified configuration and subsequent retraction of the insertion needle from the access tube, the terminal segment will return to the native configuration and fluid flow through the internal passage will be facilitated by the gradually expanded configuration of the internal passage of the tubular wall of the access tube.

2. The system of claim 1 wherein the internal diameter of the orifice is at least about twice the outside diameter of the access tube.

3. The system of claim 1 wherein the terminal segment, when in the modified configuration, is tapered from the outside diameter of the tubular wall toward the nominal internal diameter and the insertion point of the insertion needle.

4. The system of claim 3 including a fitting affixed to the access tube adjacent the proximal end of the access tube, and wherein the access tube has an overall length between the fitting and the terminal end, the prescribed length of the terminal segment is approximately two-thirds of the overall length, and the modified configuration is tapered along the entire prescribed length.

5. The system of claim 4 wherein the internal diameter of the orifice is at least about twice the outside diameter of the access tube.

6. The system of claim 1 wherein the terminal segment, in the native configuration, is flared radially outwardly along the prescribed length.

7. The system of claim 1 including a check valve communicating serially with the internal passage of the access tube and responsive to withdrawal of the insertion needle to preclude the flow of fluid through the internal passage upon withdrawal of the insertion needle.

8. The system of claim 1 including at least one securing tab integral with the access tube and carrying an adhesive layer in place for selective securement of the tab, and the access tube, upon gaining intravascular access.

9. The system of claim 8 including a release sheet juxtaposed with the adhesive layer.

10. A method for facilitating percutaneous intravascular access while militating against unwanted penetration of an accessed blood vessel, the method comprising:
   providing an insertion needle having a given diameter and terminating in an insertion point;
   providing an access tube having a tubular wall with a terminal end, an outside diameter and an internal passage with a nominal internal diameter complementary to the given diameter of the insertion needle;
   constructing at least a terminal segment of the tubular wall of the access tube adjacent the terminal end to be comprised of a shape memory polymer, with the terminal segment having a prescribed length and a native configuration wherein the internal passage increases radially outwardly along the terminal segment toward the terminal end to provide the internal passage with a gradually expanding configuration including an orifice at the terminal end having an internal diameter greater than the nominal internal diameter;

modifying the terminal segment to conform the terminal segment to a modified configuration wherein the terminal segment will be substantially contiguous with the insertion needle along the prescribed length and the terminal end will be juxtaposed with the penetrating point to facilitate insertion while militating against unwanted penetration;

locating the insertion needle within the internal passage of the access tube with the terminal end of the access tube juxtaposed with the insertion point of the insertion needle when the terminal segment is in the modified configuration;

inserting the insertion point and the juxtaposed terminal segment in the modified configuration into a blood vessel until the insertion point is just within the blood vessel;

advancing the access tube into the blood vessel while maintaining the insertion needle substantially stationary;

subsequently retracting the insertion needle from the access tube; and effecting transformation of the terminal segment in response to an external condition to return the terminal segment from the modified configuration to the native configuration such that the terminal segment will return to the native configuration, placed within the accessed blood vessel, and volumetric fluid flow through the internal passage will be facilitated by the radially outwardly increasing configuration of the internal passage of the tubular wall of the access tube.

11. The method of claim 10 including constructing the internal diameter of the orifice to be at least about twice the outside diameter of the tubular wall.

12. The method of claim 10 including tapering the modified configuration from the outside diameter of the tubular wall toward the nominal internal diameter adjacent the terminal end.

13. The method of claim 10 including constructing the internal diameter of the orifice to be at least about twice the outside diameter of the tubular wall, and tapering the modified configuration along the prescribed length of the terminal segment.

14. The method of claim 10 including constructing the terminal segment of the tubular wall such that, in the native configuration, the terminal segment is flared radially outwardly toward the terminal end of the access tube, along the prescribed length.

15. An improvement in a system for facilitating percutaneous intravascular access by an insertion needle having a given diameter and terminating in an insertion point, while militating against unwanted penetration of an accessed blood vessel, the improvement comprising:

an access tube having a tubular wall with an outside diameter, a proximal end, a distal terminal end, and an internal passage having a nominal internal diameter complementary to the given diameter of the insertion needle for reception of the insertion needle within the access tube, with the insertion needle extending to the terminal end;

the tubular wall including at least a terminal segment comprised of a shape memory polymer, the terminal segment having a prescribed length extending to the terminal end of the access tube and being conformable between a native configuration wherein the internal passage increases radially outwardly along the terminal segment toward the terminal end to provide the internal passage with a gradually expanded configuration including an orifice at the terminal end having an internal diameter greater than the nominal internal diameter, and a modified configuration wherein the terminal segment will be substantially contiguous with the insertion needle along the prescribed length and the terminal end will be juxtaposed with the insertion point of the insertion needle to facilitate insertion while militating against unwanted penetration;

the terminal segment being transformable in response to an external condition to return from the modified configuration to the native configuration such that upon insertion into the blood vessel of the terminal segment in the modified configuration, the terminal segment will return to the native configuration and fluid flow through the internal passage will be facilitated by the gradually expanded configuration of the internal passage of the tubular wall of the access tube.

16. The improvement of claim 15 wherein the internal diameter of the orifice is at least about twice the outside diameter of the access tube.

17. The improvement of claim 15 wherein the terminal segment, when in the modified configuration, is tapered from the outside diameter of the tubular wall toward the nominal internal diameter at the terminal end of the access tube.

18. The improvement of claim 17 including a fitting affixed to the access tube adjacent the proximal end of the access tube, and wherein the access tube has an overall length between the fitting and the terminal end, the prescribed length of the terminal segment is approximately two-thirds of the overall length, and the modified configuration is tapered along the entire prescribed length.

19. The improvement of claim 18 wherein the internal diameter of the orifice is at least about twice the outside diameter of the access tube.

20. The improvement of claim 15 wherein the terminal segment, in the native configuration, is flared radially outwardly along the prescribed length.

21. The improvement of claim 15 including at least one securing tab integral with the access tube and carrying an adhesive layer in place for selective securement of the tab, and the access tube, upon gaining intravascular access.

22. The improvement of claim 21 including a release sheet juxtaposed with the adhesive layer.

23. The improvement of claim 15 including a fitting affixed to the access tube adjacent the proximal end of the access tube, and wherein the access tube has an overall length between the fitting and the terminal end, and the prescribed length of the terminal segment is approximately two-thirds of the overall length of the access tube.

* * * * *